(12) United States Patent
Wycech

(10) Patent No.: US 6,233,826 B1
(45) Date of Patent: May 22, 2001

(54) METHOD FOR REINFORCING STRUCTURAL MEMBERS

(76) Inventor: Joseph S Wycech, 795 Hidden La., Grosse Pointe Woods, MI (US) 48236-1522

(*) Notice: Subject to any disclaimer, the term of this patent is extended or adjusted under 35 U.S.C. 154(b) by 0 days.

(21) Appl. No.: 09/103,033

(22) Filed: Jun. 23, 1998

Related U.S. Application Data

(60) Provisional application No. 60/053,264, filed on Jul. 21, 1997.

(51) Int. Cl.$^7$ ........................................... B23P 6/00
(52) U.S. Cl. .................. 29/897.1; 29/897.2; 29/897.35; 29/402.09; 29/402.18; 29/530; 52/309.14; 52/309.15; 52/737.4; 52/735.1
(58) Field of Search ................... 29/897.1, 897, 29/897.2, 897.35, 469.5, 530, 402.09, 402.18, 464, 466, 468, 447, 890.031, 727, 723; 264/46.9, 46.5; 138/93, 95; 52/309.8, 309.14, 309.15, 731.2, 732.1, 738.1, 737.4, 736.3, 735.1, 82, 86

(56) References Cited

U.S. PATENT DOCUMENTS

| | | | |
|---|---|---|---|
| Re. 30,802 | * 11/1981 | Rogers, Jr. | 29/402.09 |
| Re. 34,978 | * 6/1995 | Adams et al. | 29/468 |
| 1,993,307 | * 3/1935 | Nicholson | 138/89 |
| 3,123,170 | 3/1964 | Bryant . | |
| 3,493,257 | 2/1970 | Fitzgerald et al. . | |
| 4,090,734 | 5/1978 | Iami et al. . | |
| 4,186,162 | 1/1980 | Daley . | |
| 4,238,540 | 12/1980 | Yates et al. . | |
| 4,397,490 | 8/1983 | Evans . | |
| 4,436,120 | * 3/1984 | Josien et al. | 138/93 |
| 4,484,386 | * 11/1984 | Stonitsch | 264/46.5 |
| 4,559,274 | 12/1985 | Kloppe et al. . | |
| 4,610,836 | 9/1986 | Wycech . | |
| 4,640,150 | * 2/1987 | Kobayashi et al. | 264/46.9 |
| 4,751,249 | 6/1988 | Wycech . | |
| 4,783,890 | * 11/1988 | Gaudin | 29/402.09 |
| 4,836,516 | 6/1989 | Wycech . | |
| 4,853,270 | 8/1989 | Wycech . | |
| 4,861,097 | 8/1989 | Wycech . | |
| 4,901,500 | 2/1990 | Wycech . | |
| 4,908,930 | 3/1990 | Wycech . | |

(List continued on next page.)

FOREIGN PATENT DOCUMENTS

| | | |
|---|---|---|
| 29 19 049A | 11/1980 | (DE) . |
| 90 11 147.8 | 12/1990 | (DE) . |
| 4203460 | 8/1992 | (DE) . |
| 93 20 333.0 | 7/1994 | (DE) . |
| 0 061 131 | 9/1982 | (EP) . |
| 0 414 302 A1 | 2/1991 | (EP) . |
| 0 453 777 A2 | 10/1991 | (EP) . |
| 628868 | 3/1947 | (GB) . |
| 2061 196 | 5/1981 | (GB) . |
| 2197 267 | 5/1988 | (GB) . |
| 01069308 | 3/1989 | (JP) . |
| 01069309 | 3/1989 | (JP) . |
| 02206537 | 8/1990 | (JP) . |
| 5389920 | 2/1993 | (JP) . |
| WO 89/06595 | 7/1989 | (WO) . |
| WO 93/05103 | 3/1993 | (WO) . |

*Primary Examiner*—T Cuda Rosenbaum
*Assistant Examiner*—Trinh Nguyen
(74) *Attorney, Agent, or Firm*—Wayne C. Jaeschke; Stephen D. Harper; Harold Pezzner

(57) ABSTRACT

A method for reinforcing a selected portion of a structural part utilizes a flexible tube having a unexpanded, preferably thermally expandable resin sheath. The sheath may be limited to a selected region along the length of the flexible tube. The flexible tube is inserted through a curved passage and conforms to the geometry of the part to be reinforced. After the portion of the tube having the sheath reaches the desired location, the tube is secured in place. Upon heating, the resin expands to several times its original volume and fills the structural cavity only at that region.

28 Claims, 1 Drawing Sheet

U.S. PATENT DOCUMENTS

| | | |
|---|---|---|
| 4,922,596 | 5/1990 | Wycech . |
| 4,923,902 | 5/1990 | Wycech . |
| 4,936,004 * | 6/1990 | Vaughn .................................. 29/468 |
| 4,978,562 | 12/1990 | Wycech . |
| 4,995,545 | 2/1991 | Wycech . |
| 5,040,283 * | 8/1991 | Pelgrom ........................... 29/402.09 |
| 5,122,398 | 6/1992 | Seiler et al. . |
| 5,124,186 | 6/1992 | Wycech . |
| 5,194,199 | 3/1993 | Thum . |
| 5,199,463 * | 4/1993 | Lippiatt .................................. 138/93 |
| 5,242,637 * | 9/1993 | Inoue et al. ......................... 264/45.3 |
| 5,255,487 | 10/1993 | Weiting et al. . |
| 5,474,721 * | 12/1995 | Stevens ............................... 264/46.9 |
| 5,575,526 * | 11/1996 | Wycech ................................ 296/205 |
| 5,665,295 * | 9/1997 | Takamoto et al. .............. 264/172.19 |
| 5,884,960 * | 3/1999 | Wycech ............................ 296/146.6 |
| 5,885,494 * | 3/1999 | Venkataraman et al. ........... 264/46.5 |

* cited by examiner

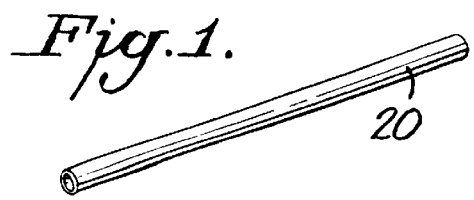
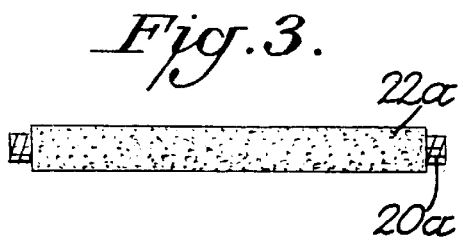
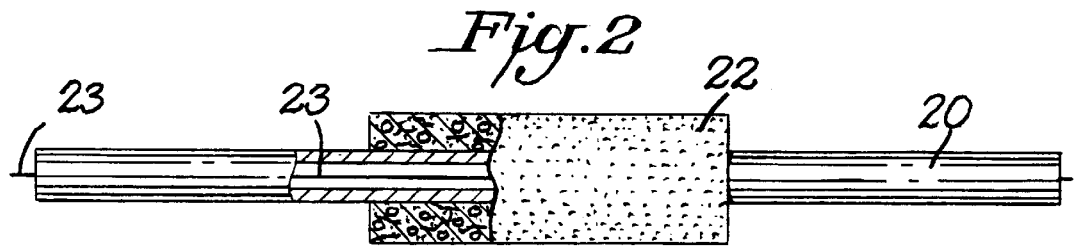
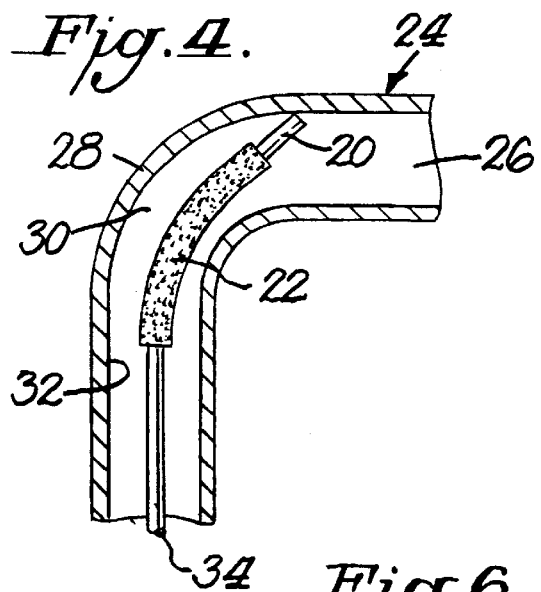
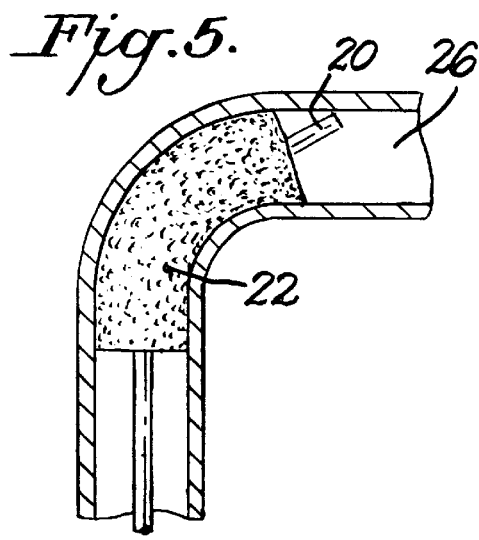
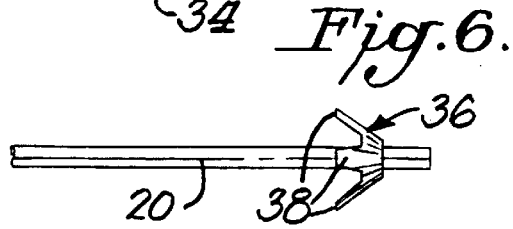
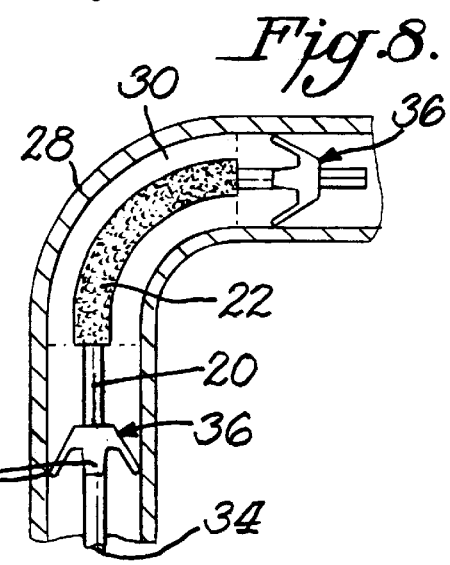
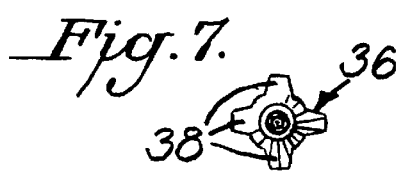

METHOD FOR REINFORCING STRUCTURAL MEMBERS

CROSS REFERENCE TO RELATED APPLICATION

This application is based on provisional application Ser. No. 60/053,264, filed Jul. 21, 1997.

FIELD OF THE INVENTION

The present invention relates generally to the reinforcement of hollow structural members and more specifically deals with reinforcement of structures having enclosed regions that present special access problems.

BACKGROUND OF THE INVENTION

In recent years, a number of factors have necessitated fundamental changes in the approach to automotive structural design. These include the need to meet ever-increasing impact resistance and fuel economy standards and the need to produce a competitively priced vehicle in a global marketplace. At times, these requirements are seemingly at odds with one another. For example, impact resistance can in most cases be achieved simply by increasing steel thickness or through the use of high strength steels. These approaches, however, generally increase vehicle weight and/or cost. Although light-weight resins are available which can be used to fill entire hollow cavities of structural members to provide greater strength, these materials are expensive and thus their use in great quantities undesirably increases vehicle cost.

The present inventor has pioneered a novel approach to structural part reinforcement through localized reinforcement of critical regions using microsphere-filled thermally expandable resins, such as: a composite door beam which has a resin-based core that occupies not more than one-third of the bore of a metal tube; a hollow laminate beam characterized by high stiffness-to-mass ratio and having an outer portion which is separated from an inner tube by a thin layer of structural foam, a W-shaped carrier insert reinforcement which carries a foam body for use in reinforcing a hollow beam; a bulkhead that utilizes a thermally expandable foam to provide localized reinforcement of a rail for the attachment of an engine cradle or the like.

Although these techniques are well suited for a number of applications, there exists a need for localized reinforcement of regions having special access problems. More specifically, in a number of hollow structural parts the member has an enclosed region or space which is located some distance from the opening of the space and is difficult to reach due to a curvature or bend in the member. In some instances the member and the channel which it defines have an irregular geometry that makes access to a particular internal region difficult. Of course, in some instances it may be possible to simply fill the entire structure with a liquid resin which is then cured, but as stated above, this approach may be prohibitively expense in a number of applications. Accordingly, there is a need for an alternative method of providing localized reinforcement of such parts. The present invention provides a solution to this problem.

It is an object of the present invention to provide a method of providing a local reinforcement in a region of a hollow structural part which is difficult to reach using conventional techniques.

It is a further object of the present invention to provide a method of introducing a localized resin reinforcement in a structural part where the region to be reinforced is beyond a curvature in a channel.

It is still a further object of the present invention to provide a method of centralizing a resin reinforcement in a hollow structural part in a region which is difficult to access.

SUMMARY OF THE INVENTION

In one aspect the present invention provides a method of reinforcing a part in a localized region. The method includes the steps of providing a flexible member having a length substantially greater than its width; covering at least a portion of the flexible member with a thermally expandable resin; and inserting the flexible member into the cavity of a hollow structural part. The insertion step includes the step of bending the flexible member to accommodate the geometry of the part cavity. The resin is then thermally expanded such that the resin is bonded to the structural part. In this manner, localized reinforcement can be achieved for any number of parts whose internal geometry would make it difficult or impossible to reinforce using conventional techniques.

In one aspect, the flexible member is a tube around which the resin is applied as a layer or coating. The resin-coated tube is then inserted in the structural part and bends as pressure is applied such that it can be fed into the part cavity, i.e. it conforms to the desired shape as it is inserted into the part.

In one aspect, the resin includes a blowing agent and glass microspheres. After the flexible member is in place in the part, the part is heated, for example after installation in a motor vehicle, to a temperature sufficient to activate the blowing agent and thermally expand the resin. As the resin expands it bonds to the inner walls of the part forming a tube-in-tube type structure with high strength characteristics.

In one aspect, the thermally expanded resin includes, in parts by weight, from about 40% to about 80% resin, from about 10% to about 50% microspheres, from about 0.5% to about 5% blowing agent, from about 1% to about 15% filler, from about 0.5% to about 2% accelerator and from about 1% to about 8% curing agent.

In still another aspect, the flexible member includes one or more stand-offs which space it from the inner walls of the structural part.

These and other aspects, features and objects of the invention will be more fully described in the following detailed description of the preferred embodiments of the invention with reference to the drawings.

BRIEF DESCRIPTION OF THE DRAWINGS

FIG. 1 illustrates a resin support tube used in the method of the present invention.

FIG. 2 illustrates a side elevational view partly in section showing the position of the unexpanded resin on the resin support tube.

FIG. 3 illustrates another resin support tube with a covering of unexpanded resin.

FIG. 4 depicts a curved structural member in cross-section to reveal the resin support tube in position prior to expansion of the resin.

FIG. 5 depicts the curved structural member of FIG. 4 in cross-section, revealing the expanded resin forming an internal reinforcement.

FIG. 6 is a front view of a resin support tube having radial stand-offs for use in the present invention.

FIG. 7 is an end view of the support tube of FIG. 6 in the direction of arrow 7—7.

FIG. 8 depicts a curved structural member in cross-section, revealing the unexpanded resin and the placement of the stand-offs.

DETAILED DESCRIPTION OF THE PREFERRED EMBODIMENTS OF THE INVENTION

Referring to FIGS. 1 and 2 of the drawings, flexible member or tube 20 is shown which serves as a support for unexpanded resin sheath 22. Flexible member 20 is most preferably a hollow tube similar to that used as a conduit for electrical wiring 23. Various flexible conduits will be known to those skilled in the art. One particular preferred flexible conduit is a metallic spiral tube which can be flexed without metal deformation due to its spiral construction. Of course, it may not be necessary for tube 20 to be round in cross section and other configurations such as square or oval may be suitable. Where flexible member 20 is a hollow metal tube it will typically be formed of aluminum and will preferably have a wall thickness of from about 0.5 to about 1.2 mm. The diameter of tube 20 will vary depending upon the application, but will typically be from about 8 to about 40 mm and will typically have a length of from about 50 to about 800 and preferably 200 mm in most automotive applications. In some applications, tube 20 will be deformed beyond its elastic limit during placement in the structure to be reinforced. In addition, in some applications a more elastic tube or rod can be used which is essentially spring biased in position in the structural cavity. Although hollow tube 20 is most preferred, particularly since it provides a lightweight structure, solid rods may also be used. It may be desirable to use plastic rods or tubes, rather than metal, as tube 20 in some applications.

The length of tube 20 is a function of the distance to the site to be reinforced from the cavity opening. The length of tube 20 is greater than its diameter or width and in many applications tube 20 will be preferably at least 5 times or may be 20 times and often more than 100 times longer than its diameter in cross section. In many applications, tube 20 will have a length of from about 50 to about 200 mm. Also, in some applications, it may be desirable to cover substantially all of tube 20a, shown as a spiral conduit in FIG. 3, with resin sheath 22a.

Resin sheath 22 in most applications will be a layer extending around the entire outer surface of tube 20 and will usually be of relatively uniform thickness, for example from about 2 to about 6 or to about 8 mm, in the unexpanded state. Resin sheath 22 can be prepared by die cutting a sheet of resin to the requisite geometry and the wrapping the pre-cut sheet around tube 20. Alternatively, the coating may be molded on the carrier, although it may be possible to use other forms of coating, such as by spraying or the like.

The polymer used to form resin sheath 22 is a resin based material which is preferably thermally expandable. A number of resin-based compositions can be utilized to form resin sheath 22 in the present invention. The preferred compositions impart excellent strength and stiffness characteristics while adding only marginally to the weight. With specific reference now to the composition of sheath 22, the density of the material should preferably be from about 20 pounds per cubic feet to about 50 pounds per cubic feet to minimize weight. The melting point, heat distortion temperature and the temperature at which chemical breakdown occurs must also be sufficiently high such that sheath 22 maintains its structure at high temperatures typically encountered in pain ovens and the like. Therefore, sheath 22 should be able to withstand temperatures in excess of 320 degrees F. and preferably 350 degrees F. for short times. Also, sheath 22 should be able to withstand heats of about 90 degrees F. to 200 degrees F. for extended periods without exhibiting substantial heat-induced distortion or degradation.

In more detail, in one particularly preferred embodiment the thermally expanded structural foam of sheath 22 includes a synthetic resin, a cell-forming agent, and a filler. A synthetic resin comprises from about 40 percent to about 80 percent by weight, preferably from about 45 percent to about 75 percent by weight, and most preferably from about 50 percent to about 70 percent by weight of sheath 22. Most preferably, a portion of the resin includes a flexible epoxy. As used herein, the term "cell-forming agent" refers generally to agents which produce bubbles, pores, or cavities in sheath 22. That is, sheath 22 has a cellular structure, having numerous cells disposed throughout its mass. This cellular structure provides a low-density, high-strength material, which provide a strong, yet lightweight structure. Cell-forming agents which are compatible with the present invention include reinforcing "hollow" microspheres or microbubbles which may be formed of either glass or plastic. Glass microspheres are particularly preferred. Also, the cell-forming agent may comprise a blowing agent which may be either a chemical blowing agent or a physical blowing agent. Where the cell-forming agent comprises microspheres or macrospheres, it constitutes from about 10 percent to about 50 percent by weight, preferably from about 15 percent to about 45 percent by weight, and most preferably from 20 percent to about 40 percent by weight of the material which forms sheath 22. Where the cell-forming agent comprises a blowing agent, it constitutes from about 0.5 percent to about 5.0 percent by weight, preferably from about 1 percent to about 4.0 percent by weight, and most preferably from about 1 percent to about 2 percent by weight of sheath 22. Suitable fillers include glass or plastic microspheres, fumed silica, calcium carbonate, milled glass fiber, and chopped glass strand. A thixotropic filler is particularly preferred. Other materials may be suitable. A filler comprises a from about 1 percent to about 15 percent by weight, preferably from about 2 percent to about 10 percent by weight and most preferably from about 3 percent to about 8 percent y weight of sheath 22.

Preferred synthetic resins for use in the present invention include thermosets such as epoxy resins, vinyl ester resins, thermoset polyester resins, and urethane resins. It is not intended that the scope of the present invention be limited by molecular weight of the resin and suitable weights will be understood by those skilled in the art based on the present disclosure. Where the resin component of the liquid filler material is a thermoset resin, various accelerators, such as imidizoles and curing agents, preferably dicyandiamide may also be included to enhance the cure rate. A functional amount of accelerator is typically from about 0.5 percent to about 2.0 percent of the resin weight with corresponding reduction in one of the three components, resin, cell-forming agent or filler. Similarly, the amount of curing agent used is typically from about 1 percent to about 8 percent of the resin weight with a corresponding reduction in one of the three components, resin, cell-forming agent or filler. Effective amounts of processing aids, stabilizers, colorants, UV absorbers and the like may also be included in layer. Thermoplastics may also be suitable.

In the following table, a preferred formulation for sheath 22 is set forth. It has been found that this formulation provides a material which fully expands and cures at about 320 degrees F. and provides excellent structural properties. All percentages in the present disclosure are percent by weight unless otherwise specifically designated.

| INGREDIENT | PERCENTAGE BY WEIGHT |
| --- | --- |
| EPON 828 (epoxy resin) | 37.0 |
| DER 331 (flexible epoxy resin) | 18.0 |
| DI-CY (dicyandiamide curing agent) | 4.0 |
| IMIDIZOLE (accelerator) | 0.8 |
| FUMED SILICA (thixotropic filler) | 1.1 |
| CELOGEN AZ199 (azodicarbonamide blowing agent) | 1.2 |
| B38 MICROS (glass microspheres) | 37.0 |
| WINNOFIL CALCIUM CARBONATE ($C_aCO_3$ filler) | 0.9 |

Referring now to FIG. 4 of the drawings, structural part 24 is seen in cross section and defines cavity 26. For the purpose of illustration only, structural part 24 is shown here as a portion of an automotive roll bar. Other preferred applications are for use in reinforcing top A-pillar joints and seat frames. Structural part 24 has an arcuate or curved portion 28 which defines an arcuate portion 30 of cavity 26. Cavities similar to cavity 26, i.e. those which are difficult to access, are the focus of the present invention. Flexible tube 20 is shown in position in cavity 26 prior to thermal expansion of the resin. Tube 20 is bent to conform to the shape of cavity 26. This shaping operation is preferably performed in place. In other words, flexible tube 20, having resin sheath 22 positioned at a preselected location relative to the ends of tube 20, in inserted into cavity 26. As force is applied to tube 20 it moves farther through the passage. As it encounters resistance from the inner walls 32, flexible tube 20 bends, thereby "snaking" its way through cavity 26, including beyond arcuate portion 30. Alternatively, it may be possible in some applications to bend tube 20 to a conforming geometry prior to inserting it into cavity 26. Flexible tube 20 is inserted a distance sufficient to bring resin sheath 22 into position at arcuate portion 28. Once in position, outer end 34 or tube 20 is clamped into position relative to tube 20 with a clamp (not shown) or otherwise fixed in position, if required.

The cavity 26 is of non-straight linear geometry which could be more complicated than having simply one bend with its arcuate portion such as illustrated in FIG. 4. Where there are multiple bends or irregularities a resin sheath 22 could be provided for some or all of these irregularities, this could be done by providing individual spaced resin sections or by providing one or more continuous resin sections which are located at two or more bends.

Referring now to FIG. 5 of the drawings, resin 22 is shown in the expanded state. That is, once tube 20 and resin 22 are in position in structural part 24, the resin is expanded by heating the entire assembly to a temperature which activates the blowing agent to expand and cure resin sheath 22. In automotive applications that is typically achieved as the vehicle moves through the paint oven. Resin 22 expands to several times its original volume, preferably at least twice its original volume. The expanded resin contacts and bonds firmly to surrounding walls 32 of structural part 24. It also cures to form a rigid reinforcement in part 24. In this manner, a minimum amount of resin is used at the precise location where reinforcement is required.

Referring now to FIGS. 6 and 7 of the drawings, tube 20 is provided with radical stand-off assembly 36 which has legs 38, typically two to four in number. As seen in FIG. 8, stand-off assembly 36 serves the function of generally centering tube 20 in structural part 24. It may be preferable to make legs 38 somewhat resilient, i.e. it may be desirable to allow legs 38 to flex inwardly as tube 20 is inserted into cavity 26.

While the invention has been described primarily in connection with automotive or vehicle parts, it is to be understood that the invention may be practiced as part of other products, such as aircrafts, ships, bicycles or virtually anything that requires energy for movement. Similarly, the invention may be used with stationary or static structures, such as buildings, to provide a rigid support when subjected to vibration such as from an earthquake ro simply to provide a lightweight support for structures subjected to loads. Additionally, while the invention has been described primarily with respect to heat expandable foams and with respect to metal parts such as the structural part and the flexible member, other materials can be used. For example, the foam could be any suitable known expandable foam which is chemically activated into expansion and forms a rigid structural foam. The flexible member could be made of materials other than metal such as various plastics or polymeric materials or various wood type fibrous materials having sufficient rigidity to function as a back drop or support for the foam. Where a heat expandable foam is used the flexible member should be able to withstand the heat encountered during the heat curing. Where other types of foam materials are used, however, it is not necessary that the flexible member be able to withstand high temperatures. Instead, the basic requirement for the flexible member is that it have sufficient rigidity to function in its intended manner. It is also possible, for example, to use as the flexible member materials which in themselves be come rigid upon curing or further treatment. The invention may also be practiced where the structural part is made of materials other than metal. It is preferred, however, that materials be selected for the structural part and flexible member, as well as the foam, so that the thin unexpanded foam upon expansion forms a strong bond with the structural part and flexible member, so that a structural composition will result.

While particular embodiments of this invention are shown and described herein, it will be understood, of course, that the invention is not be limited thereto since many modifications may be made, particularly by those skilled in this art, in light of this disclosure. It is contemplated, therefore, by the appended claims, to cover any such modifications as fall within the true spirit and scope of this invention.

What is claimed is:

1. A method of reinforcing a part, comprising the steps of: providing a flexible member having a length greater than its width; covering at least a portion of the flexible member with an expandable resin mounted directly on the flexible member; inserting the flexible member with the expandable resin into a cavity of a hollow part, the inserting step including the step of bending the flexible member with the expandable resin to accommodate the geometry of the cavity while the resin is of smaller outside dimension than the inside dimension of the part whereby the flexible member and the resin move freely through the part without the resin and the portion of the flexible member having the resin mounted thereon contacting the inside dimension of the part; and expanding the expandable resin into contact with the inside dimension of the part and thereby bonding the resin to the part.

2. The method of reinforcing a part recited in claim 1, wherein the flexible member is a hollow tube.

3. The method of reinforcing a part recited in claim 1, wherein the flexible member is a solid rod.

4. The method of reinforcing a part recited in claim 1, wherein resin is thermally expandable and contains hollow microspheres.

5. The method of reinforcing a part recited in claim 1, wherein the part is selected from the group consisting of an A-pillar joint and a seat frame and a roll-bar for a motor vehicle.

6. The method of reinforcing a part recited in claim 1, wherein the flexible member has an attached spacer for spacing the flexible member from the inner walls of the part prior to the expansion step.

7. The method of reinforcing a part recited in claim 1, wherein the length of the flexible tube is at least five times its diameter.

8. The method of reinforcing a part recited in claim 1, wherein the diameter of the flexible tube is between about 8 and about 40 mm and its length is from about 50 to about 200 mm.

9. The method of reinforcing a part recited in claim 1, wherein the expandable resin forms a layer encircling and encasing at least a portion of the flexible member.

10. The method of reinforcing a part recited in claim 1, wherein the resin before expansion is a layer which has a uniform thickness of from about 2 to about 8 mm.

11. The method of reinforcing a part recited in claim 1, wherein the flexible member is hollow and has a wall thickness of from about 0.5 to about 1.2 mm.

12. The method of reinforcing a part recited in claim 1, wherein the flexible tube is formed of metal.

13. The method of reinforcing a part recited in claim 12, wherein the metal is aluminum.

14. The method of reinforcing a part recited in claim 1, wherein the flexible member is inelastically deformed prior to the insertion step and forms a deformation of the flexible member that conforms to the geometry of the cavity.

15. The method of reinforcing a part recited in claim 1, wherein the flexible member is shaped during the insertion step by contact with the part.

16. The method of reinforcing a part recited in claim 1, wherein the flexible member is secured in the part prior to the expansion step.

17. The method of reinforcing a part recited in claim 1, wherein the length of the flexible member is at least five times its width.

18. The method of reinforcing a part recited in claim 1, wherein substantially all of the flexible tube is covered by the expandable resin.

19. The method of reinforcing a part recited in claim 1, wherein the resin is thermally expandable and includes, percentage by weight, from about 40% to about 80% resin, from about 10% to about 50% microspheres, from about 0.5% to about 5% blowing agent, from about 1% to about 15% filler, from about 0.5% to about 2% accelerator and from about 1% to about 8% curing agent.

20. The method of reinforcing a part recited in claim 1, wherein the resin is thermally expandable and includes, percentage by weight, 55% epoxy resin, 4% dicyandiamide curing agent, 0.8% imidizole accelerator, 1.1% fumed silica, 1.2% azodicarbonamide blowing agent, 37% glass microspheres, and 0.9% calcium carbonate filler.

21. The method of reinforcing a part recited in claim 1, wherein the flexible member is a hollow tube with electrical wiring extending longitudinally therein.

22. The method of reinforcing a part recited in claim 1, wherein the cavity is of non-straight linear geometry having at least one bend, and snaking the flexible member through the cavity until the resin is located at the bend.

23. The method of reinforcing a part recited in claim 22, wherein there are a plurality of bends, and locating resin at more than one of the bends.

24. The method of reinforcing a part recited in claim 1, wherein the resin is in a form of a sheet which is cut by a die and wrapped around the flexible member.

25. The method of reinforcing a part recited in claim 1, wherein the flexible member is a spiral wrapped tube.

26. The method of reinforcing a part recited in claim 1, wherein the part is a vehicle part, the resin being thermally expandable, and expanding the resin in a vehicle paint oven during a painting step.

27. A method of reinforcing a structural part having a space which is difficult to access due to the geometry of the part, comprising the steps of: providing a hollow flexible member having a length at least five times its width; coating at least a portion of the flexible member with an expandable resin; inserting the flexible member with the expandable resin into the cavity of a hollow structural part, the inserting step including the step of bending the flexible member with the expandable resin to accommodate the geometry of said cavity while the resin is of smaller outside dimension than the inside dimension of the structural part whereby the flexible member and the resin move freely through the structural part without the resin and the portion of the flexible member having the resin mounted thereon contacting the inside dimension of the structural part; securing the flexible member with the expandable resin in the structural part by expanding the expandable resin into contact with the inside dimension of the structural part and thereby bonding the resin to the structural part.

28. The method of reinforcing a part recited in claim 1, wherein the resin is a coating molded onto the flexible member.

* * * * *

UNITED STATES PATENT AND TRADEMARK OFFICE
CERTIFICATE OF CORRECTION

PATENT NO. : 6,233,826 B1  Page 1 of 1
DATED : May 22, 2001
INVENTOR(S) : Wycech It is certified that error appears in the above-identified patent and that said Letters Patent is hereby corrected as shown below:

<u>Title page,</u>
Below Inventors, and above [*] Notice, insert therefor Item:
-- [73] Assignee: Henkel Corporation, Gulph Mills, PA (US) --.

Signed and Sealed this

First Day of June, 2004

JON W. DUDAS
*Acting Director of the United States Patent and Trademark Office*